(12) United States Patent
Böhringer et al.

(10) Patent No.: US 12,082,884 B2
(45) Date of Patent: Sep. 10, 2024

(54) REGISTRATION AND IDENTIFICATION TOOL AND METHOD FOR A DENTAL AND/OR CRANIO-MAXILLOFACIAL SURGICAL INSTRUMENT AND/OR GENERAL SURGICAL INSTRUMENT

(71) Applicant: MININAVIDENT AG, Liestal (CH)

(72) Inventors: Stephan Böhringer, Weil am Rhein (DE); Frank Berlinghoff, Munich (DE); Michael Breitenstein, Wenslingen (CH); Philipp Jürgens, Weil am Rhein (DE); Erik Schkommodau, Liestal (CH)

(73) Assignee: MININAVIDENT AG, Liestal (CH)

( * ) Notice: Subject to any disclaimer, the term of this patent is extended or adjusted under 35 U.S.C. 154(b) by 413 days.

(21) Appl. No.: 16/496,349

(22) PCT Filed: Mar. 20, 2017

(86) PCT No.: PCT/EP2017/056585
§ 371 (c)(1),
(2) Date: Sep. 20, 2019

(87) PCT Pub. No.: WO2018/171862
PCT Pub. Date: Sep. 27, 2018

(65) Prior Publication Data
US 2020/0046454 A1 Feb. 13, 2020

(51) Int. Cl.
*A61B 34/20* (2016.01)
*A61C 1/00* (2006.01)
(Continued)

(52) U.S. Cl.
CPC ............ *A61B 34/20* (2016.02); *A61C 1/0007* (2013.01); *A61C 3/02* (2013.01);
(Continued)

(58) Field of Classification Search
CPC .... A61B 2017/00725; A61B 2034/207; A61B 2090/3937
See application file for complete search history.

(56) References Cited

U.S. PATENT DOCUMENTS

| 6,988,009 | B2 * | 1/2006 | Grimm | ................. A61F 2/4607 606/102 |
| 2004/0039402 | A1 * | 2/2004 | Zeiss | ..................... A61B 34/20 606/130 |

(Continued)

FOREIGN PATENT DOCUMENTS

| JP | 2004-529679 A | 9/2004 |
| JP | 2005-279263 A | 10/2005 |

(Continued)

*Primary Examiner* — Jason M Ip
(74) *Attorney, Agent, or Firm* — Seed IP Law Group

(57) ABSTRACT

A registration and identification tool (1) for an instrument (100), comprising a body (2), a marker member (3) which is optically detectable and provided on the body (2), and a recess (4) in the body (2) which extends from an outer surface of the body (2) into the inside of the body (2), thereby defining an extension direction of the recess (4), wherein the recess (4) has a shape such that a lateral extension of the recess (4) decreases in the direction from the outer surface of the body (2) towards the inside of the body (2). A method for registration and identification of an instrument (100) comprising by placing a surgical tool (102) of the surgical instrument (100) into the recess (4) of the tool (1), pivoting the surgical instrument (100) relative to the marker member (3) while the surgical tool (102) is placed inside the recess (4), performing a detecting process of the relative movement of the surgical instrument (100), and identifying geometrical characteristics of the surgical tool (102) and/or registering the relative position of the surgical tool (102) to the remainder of the surgical instrument (100) using the results of the detecting process.

14 Claims, 6 Drawing Sheets

(51) Int. Cl.
*A61C 3/02* (2006.01)
*A61B 17/00* (2006.01)
*A61B 90/00* (2016.01)

(52) U.S. Cl.
CPC ............ *A61B 2017/00725* (2013.01); *A61B 2034/2055* (2016.02); *A61B 2034/2057* (2016.02); *A61B 2034/207* (2016.02); *A61B 2090/3937* (2016.02); *A61C 2204/005* (2013.01)

(56) References Cited

U.S. PATENT DOCUMENTS

| | | | |
|---|---|---|---|
| 2004/0167654 A1* | 8/2004 | Grimm | A61B 90/36 700/114 |
| 2008/0077158 A1* | 3/2008 | Haider | A61B 17/1703 606/130 |
| 2011/0082467 A1 | 4/2011 | Tien et al. | |

FOREIGN PATENT DOCUMENTS

| | | |
|---|---|---|
| JP | 2008-513064 A | 5/2008 |
| WO | 2006/029541 A1 | 3/2006 |
| WO | 2015/117644 A1 | 8/2015 |

\* cited by examiner

REGISTRATION AND IDENTIFICATION TOOL AND METHOD FOR A DENTAL AND/OR CRANIO-MAXILLOFACIAL SURGICAL INSTRUMENT AND/OR GENERAL SURGICAL INSTRUMENT

FIELD OF THE INVENTION

The invention relates to a registration and identification tool for a dental and/or cranio-maxillofacial surgical instrument and/or general surgical instrument and to a method for registration and/or identification of the dental and/or cranio-maxillofacial and/or general surgical instrument, using this registration and identification tool. Further, the invention relates to a registration and identification system and a navigation system for dental and/or cranio-maxillofacial and/or general surgery, both systems comprising said registration and identification tool.

BACKGROUND ART

In recent years, surgical instruments for dental and/or cranio-maxillofacial and/or general treatment or surgery having an image photographing function for observing the inside of a mouth of a patient have been developed.

Moreover, in order to assist a surgeon during dental and/or cranio-maxillofacial treatment or surgery, navigation systems have been developed for medical navigation in which the position relationship of an instrument with respect to a part of a patient's body is ascertained.

EP 2 236 104 B1 discloses a device comprising an image output on which the surgical instrument, in particular the surgical tool, and the part of the patient's body are displayed in the correct positional relationship, and an image processor which generates a display of the part of the patient's body on the basis of virtual image data captured by means of a medical imaging method and on the basis of actual images captured during navigation. The device further comprises an image display control which displays the virtual image data on the image output primarily and as the basis of the image, wherein the actual images are superimposed on the virtual image data merely as an addition and secondarily.

The actual images are provided by a video image capture unit which is fixedly arranged on the instrument. The positional relationship of the surgical tool with respect to the part of the patient's body is ascertained by a stationary tracking system having two cameras and two reference assemblies, one assembly being placed on the part of the patient's body and the other assembly being placed on the instrument. In order to detect this positional relationship at any time during surgery, the two reference assemblies always have to be within the field of vision of the tracking system.

WO 2015/048994 A1 discloses a navigation system for dental and cranio-maxillofacial surgery, comprising a surgical handpiece, an imaging unit which is movably attached to the surgical handpiece, and a marker member which is attachable to a cranial bone, a facial bone, a tooth or teeth of a patient. The marker member comprises a plurality of marker elements which are detectable by the imaging unit. Further, a navigation method for dental and cranio-maxillofacial surgery using the navigation system is disclosed.

In order that the above described navigation systems or methods are capable of providing precise surgical navigation during dental and/or cranio-maxillofacial surgery, it is necessary to provide the systems with precise and reliable information of the geometrical characteristics of the surgical instrument, in particular the surgical tool, and the relative position of the surgical tool to the remainder of the surgical instrument. Hence, it is necessary to measure the geometrical characteristics of the surgical tool and the relative position of the surgical tool to the surgical instrument every time the surgical tool is changed. Moreover, as during the dental and/or cranio-maxillofacial surgery procedure the surgical tool might move inside a tool holder of the surgical instrument, it is also necessary to acquire or update beforementioned information during the dental and/or cranio-maxillofacial surgery procedure.

Hence, there is a need for a registration and identification tool and a method for registration and/or identification of a dental and/or cranio-maxillofacial surgical instrument and/or general surgical instrument which enable precise registration and identification of the surgical instrument, in particular of the surgical tool, in a simple and reliable manner.

SUMMARY OF THE INVENTION

One object of the invention is to provide a registration and identification tool and a method for registration and/or identification of a surgical instrument for dental and/or cranio-maxillofacial and/or general surgery which allow for precise registration and/or identification of a surgical instrument in a simple and reliable manner. Further, the invention aims to provide a registration and identification system as well as a navigation system for dental and/or cranio-maxillofacial and/or general surgery comprising said registration and identification tool.

These goals are achieved by a registration and identification tool with the technical features of claim 1, a registration and identification system with the features of claim 15, a navigation system with the features of claim 18, a method for registration and/or identification of a dental and/or cranio-maxillofacial and/or general surgical instrument with the features of claim 19 and a use of the registration and identification tool with the features of claim 21. Preferred embodiments of the invention follow from the dependent claims.

The invention provides a registration and identification tool for a dental and/or cranio-maxillofacial surgical instrument and/or general surgical instrument comprising a body, a marker member which is optically detectable, the marker member being provided on the body, and a recess in the body which extends from an outer surface of the body into the inside of the body, thereby defining an extension direction of the recess.

The recess has a shape, in particular a tapered shape, such that a lateral extension of the recess decreases in a direction from the outer surface of the body towards the inside of the body.

In the present invention the term "tapered" concerning the tapered shape of the recess defines that along the extension direction of the recess, which is an axial extension direction (or a longitudinal extension direction) of the recess and extends from the outer surface of the body substantially perpendicular to the outer surface of the body towards the inside of the body, a lateral extension of the recess decreases in the extension direction, in particular from the outer surface of the body towards the inside of the body. In other words, in case the recess has a conical shape, the diameter (inner diameter) of the recess decreases in the direction from the outer surface of the body towards the inside of the body. On the other hand, in case the recess has a so called "wedge shape", which means the recess is basically constituted by two substantially planar surfaces that are arranged opposite to each other (face each other) at an angle relative to each other, a distance between the two planar surfaces decreases along the extension direction of the recess.

Moreover, the term "lateral extension" of the recess describes an extension thereof in a plane perpendicular to the direction from the outer surface of the body towards the inside of the body, i.e., the extension direction of the recess. In case of a conical shape of the recess, as explained in detail below, the "lateral extension" corresponds to the diameter of the conus or the inner diameter or the radial extension of the conus. On the other hand, in case of Additionally, the recess or recesses could also be described as a "gauge recess", since the recess is used for identifying geometrical characteristics of a surgical tool and/or registering the relative position of the surgical tool to the surgical instrument.

Furthermore, as the recess has a shape, in particular a tapered shape, such that a lateral extension of the recess decreases in the direction from the outer surface of the body towards the inside of the body, a cylindrical, spherical or conical object, in particular a cylindrical, spherical or conical surgical tool, can only be inserted into the recess until it comes into contact with the recess at at least two points. This also applies for objects and surgical tools that have a stepped shape, wherein one or two stepped shapes are particularly preferable.

Hence, it is possible to determine or calculate the diameter of the cylindrical, spherical or conical object on the basis how deep the centre of the spherical or cylindrical object can be inserted into the recess (will be explained in detail below). In case of the cylindrical object, it is necessary that the axial direction of the cylindrical object is inserted substantially perpendicular to the extension direction of the recess.

The marker member may comprise a plurality of marker elements, which are preferably arranged in a two-dimensional pattern, thereby defining a marker member plane.

The plurality of marker elements may be separate elements or elements which are at least partly connected or joined to each other. The marker elements may be provided to the marker member so as to be separate from each other. The marker elements may be provided to the marker member so that at least some or all of the marker elements are at least partly connected or joined to each other, e.g., so as to form a continuous pattern, such as an optical pattern.

As described above, the plurality of marker elements may be arranged in a two-dimensional pattern or array, e.g., a two-dimensional optical pattern or array. The term "two-dimensional" defines that the marker elements are arranged in a common plane, which is the marker member plane. Such an arrangement of the marker elements allows for a particularly simple configuration of the marker member.

Moreover, the recess may have a conical shape in the extension direction of the recess, particularly in a direction that is substantially parallel to the marker member plane.

Forming the recess with a conical shape provides advantageous effects especially when registration and identification of a surgical tool with a spherical or conical shape is performed. Namely, when bringing a spherical or conical surface of the surgical tool into contact with the conical surface of the recess, not only a point contact can be realized, like in case of a wedge shaped recess, but a substantially line contact can be realized, in particular a substantially circular line contact. Thereby, the precision of identifying geometrical characteristics of the surgical tool and the registration of the relative position of the surgical tool to the remainder of the surgical instrument can be enhanced.

Moreover, providing the recess with an extension direction that is substantially parallel to the marker member plane is especially advantageous in combination with a conical shape of the recess, as in this case a longitudinal axis of the surgical tool, around which the surgical tool rotates during use, is substantially parallel to the marker member plane.

Further, the extension direction of the recess may be substantially perpendicular to the marker member, particularly substantially perpendicular to the marker member plane.

Providing the recess so that the extension direction of the recess is substantially perpendicular to the marker member is especially advantageous in combination with a wedge shaped recess, as in this case the longitudinal axis of the surgical tool is also substantially parallel to the marker member plane.

The body may be provided with at least two recesses, which preferably extend from the same outer surface of the body.

In this way two or more recesses with different shapes (conical, cubical, or with wedged shape) can be provided. Hence, providing the possibility to choose between different shapes of the recesses for fitting the shape of the recess to the needs of the surgical tool to be registered and/or identified.

The recess may be open to two outer surfaces of the body, which are preferably substantially perpendicular to each other.

Firstly, by opining the recess to two outer surfaces of the body, it becomes easier to insert or place the surgical tool into the recess. Secondly, during pivoting of the surgical instrument and/or during performing of a detection process, it becomes possible for a user to visually inspect or monitor the correct placement of the surgical tool in the recess. Thereby, it becomes possible to secure a correct and reliable registration and identification of the surgical tool. Finally, the manufacturing of the recess can be simplified. Moreover, the at least two recesses may have different depths from one of the two outer surfaces of the body in a direction parallel to the other one of the two outer surfaces of the body, in particular, in a direction that is perpendicular to the extension direction of the recess.

The term "depth" defines here a distance between a bottom surface of the recess and the outer surface of the body, in particular the outer surface of the body which is substantially perpendicular to the extension direction of the recess.

Accordingly, it can be avoided that a tip of the surgical tool cannot reach the bottom of the recess or the length of the tip of the cylindrical head is too long so a large part of the tip cannot be inserted into the recess, which would lead to instability and wrong measurement and/or detection results.

Further, the center of the recess or of one of the recesses may be located on or extend along a virtual line that is substantially perpendicular to the marker member plane and intersects the marker member centrically in the widthwise direction.

The positioning of the recess perpendicular to the marker member plane makes the necessary calculations for the detecting process of the relative movement of the surgical instrument The registration and identification tool may further comprise a reference pin, wherein a center of the reference pin may preferably be located on a virtual line that is perpendicular to the marker member plane and intersects the marker member centrically in the widthwise direction.

By providing the registration an identification tool with a reference pin, it becomes possible, to calibrate the surgical instrument, in particular the imaging unit of the surgical instrument. The calibration process will be described in detail below.

Further, the surgical instrument may comprise a surgical tool, in particular, a drill or a milling cutter. Moreover, the surgical tool may be a dental surgical tool. The surgical tool may be a dental drill. In particular, the surgical instrument can be used advantageously for intraoral applications, such as tooth removal or replacement, dental implants etc., using dental instruments, such as dental drills.

The marker member may be configured to be detachable from the body. Moreover, the marker member may be attachable, mountable, fixable, installable or securable to the body of the registration and identification tool. The marker member is thus configured so that it can be attached, mounted, fixed, installed or secured to the body.

Moreover, the plurality of marker elements may be configured to be detectable by an imaging unit, in particular by one or more stereoscopic camera units, and/or one or more 3D scanners, such as laser scanners, or the like.

The marker member may be provided with a first plurality of marker elements and a second plurality of marker elements which are located on two different surfaces of the marker member which are opposite to each other, particularly substantially parallel to each other.

In this way it becomes possible to identify on which side of the marker element the surgical instrument is positioned and thereby possibly identify into which recess the surgical tool is placed. This provides the possibility to adjust the routine (algorithm) which is used for registering and/or identifying the surgical tool, if necessary.

Further, the first plurality of marker elements may be arranged in a first two-dimensional pattern and the second plurality of marker elements may be arranged in a second two-dimensional pattern, wherein the first and second two-dimensional patterns are different from each other.

The invention further provides a registration and identification system for a dental and/or cranio-maxillofacial surgical instrument and/or general surgical instrument, comprising the above described registration and identification tool and an imaging unit that is configured to image the marker member, wherein the imaging unit is preferably attachable to the surgical instrument.

The imaging unit may be movably attachable, mountable or installable to the surgical instrument, so as to be movable relative to the surgical tool. The imaging unit can thus be moved independently from the surgical instrument.

The imaging unit may be movably attachable to the surgical instrument so as to be continuously, e.g., steplessly, movable relative to the instrument or the surgical tool. The imaging unit may be movably attachable to the surgical instrument so as to be movable relative to the instrument or the surgical tool in discrete steps or stages.

The imaging unit may be configured to obtain or provide imaging data, i.e., imaging data of the area in which the marker element is provided, in particular, to obtain or provide imaging date of the area where the marker element is provided in real time. Moreover, the imaging unit may be configured to detect the plurality of marker elements of the marker member. In particular, any change in the position of the surgical instrument relative to the marker member can be sensed by detecting a corresponding distortion of the two-dimensional pattern or array of the marker elements detected by the imaging unit. Hence, the relative position of the surgical instrument and the marker member can be determined in a particularly simple, reliable and precise manner, allowing a simple, reliable and precise identification of the geometrical characteristics of the surgical tool and/or registration of the relative position of the surgical tool to the remainder of the surgical instrument.

The registration and identification system may comprise a single imaging unit or a plurality of imaging units, such as two, three, four or more imaging units. The imaging units may be arrangable in different positions on the surgical instrument, e.g., along the length and/or around the circumference of the surgical instrument.

The imaging unit may comprise one or more camera units, e.g., one or more stereoscopic camera units, and/or one or more 3D scanners, such as laser scanners, or the like. The imaging unit may be capable of imaging, i.e., obtaining or providing imaging data, in the visible and/or infrared light spectrum. The imaging unit may be configured to obtain or provide three-dimensional imaging data of the area where the marker element is provided.

The 3D scanner may be a 3D surface scanner. The 3D surface scanner may be configured to optically scan the surface of the area in which the marker member, in particular the plurality of marker elements, is provided, e.g., the two-dimensional pattern of the marker elements. In this way, the relative orientation and position between the marker element and the 3D scanner and thereby the relative orientation and position between the marker element and the surgical instrument can be registered and/or monitored in a particularly precise and reliable manner.

The imaging unit may be removably attachable to the surgical instrument. In this case, the imaging unit can be removed or detached from the surgical instrument. By using such a modular configuration of the imaging unit and the surgical instrument, the imaging unit can be attached to and used in combination with different surgical instruments. Thus, a single imaging unit can be used for a variety of different surgical procedures, thereby further reducing the costs of surgery.

Moreover, the registration and identification system may further comprise a light source, such as an LED, a laser pointer or the like, which may be arranged on the imaging unit, e.g., for illuminating the marker elements of the marker member. In this way, the detection process of the marker elements by the imaging unit can be further improved.

The imaging unit may be lockable or arrestable in a plurality of discrete or continuous positions relative to the surgical instrument. In particular, the imaging unit may be movably attachable to the surgical handpiece so as to be continuously, e.g., steplessly, movable relative to the instrument and lockable in every achievable position relative to the surgical instrument.

By locking or arresting the imaging unit in a position relative to the surgical instrument, i.e., locking or arresting the imaging unit so that it is immobilised relative to the instrument, the imaging unit can be stably and robustly kept in a well-defined position relative to the surgical instrument, in particular to the surgical tool. Such an arrangement allows for a particularly precise measurement or detection of the position of the surgical instrument relative to the marker elements of the marker member.

Moreover, the registration and identification system may comprise a processing unit, storing information about the relative orientation and/or position between the marker member and the recess.

Further, the processing unit may store information about the relative orientation and/or position between the marker member and the reference pin. It is also possible that the processing unit only stores information about the relative orientation and/or positon between the marker member and the reference pin but no information about the relative orientation and/or position between the marker member and the recess.

The processing unit, such as a CPU or the like, may be configured to process imaging data of the imaging unit, i.e., imaging data obtained by the imaging unit.

The registration and identification system for a dental and/or cranio-maxillofacial surgical instrument and/or general surgical instrument of the invention is a system that uses the registration and identification tool of the invention. Therefore, the further features disclosed in connection with the above description of the registration and identification tool may also be applied to the registration and identification system of the invention.

The invention also provides a navigation system for dental and/or cranio-maxillofacial and/or general surgery, comprising the above described registration and identification tool, a surgical instrument, and an imaging unit which is attached, preferably movably attached, to the surgical instrument.

The navigation system for a dental and/or cranio-maxillofacial surgical instrument and/or general surgical instrument of the invention is a system that uses the registration and identification tool of the invention as well as the elements of the registration and identification system. Therefore, the further features disclosed in connection with the above description of the registration and identification tool and the registration and identification tool may also be applied to the registration and identification system of the invention.

Moreover, the invention provides a method for registration and/or identification of a dental and/or cranio-maxillofacial surgical instrument and/or general surgical instrument, using the above described registration and identification tool. The method comprises the steps of placing a surgical tool of the surgical instrument into the recess of the registration and identification tool, pivoting the surgical instrument relative to the marker member, while the surgical tool is placed inside the recess, performing a detecting process of the relative movement of the surgical instrument, and identifying geometrical characteristics of the surgical tool and/or registering the relative position of the surgical tool to the remainder of the surgical instrument using the results of the detecting process.

The method for registration and/or identification of a dental and/or cranio-maxillofacial surgical instrument and/or general surgical instrument may further comprise the steps of placing the surgical instrument which comprises an imaging unit onto the registration and identification tool, particularly onto a reference pin thereof, performing a detecting process, if necessary pivoting the surgical instrument during the detecting process, using the imaging unit and the marker member, calibrating of the registration and identification system, inserting of a surgical tool into the surgical instrument.

The method for registration and/or identification of a dental and/or cranio-maxillofacial surgical instrument and/or general surgical instrument of the invention provides the advantageous effects already described in detail above for the registration and identification tool of the invention. In particular, the method enables precise registration and identification of a surgical tool in a simple and reliable manner. The method allows for the relative position between the surgical tool and the marker member to be precisely determined in a simple and reliable way.

The detecting process may be performed by an imaging unit, which is preferably attached to the surgical instrument, wherein the imaging unit performs the detecting process by imaging the marker member.

The method for registration and/or identification of a dental and/or cranio-maxillofacial surgical instrument and/or general surgical instrument of the invention is a method of using the registration and identification tool or the registration and identification system of the invention. Therefore, the further features disclosed in connection with the above description of the registration and identification tool and the registration and identification system may also be applied to the method of the invention.

Moreover, the invention provides a use of the above described registration and identification tool for registration and/or identification of a dental and/or cranio-maxillofacial surgical instrument and/or general surgical instrument.

The use of the above described registration and identification tool for registration and/or identification of a dental and/or cranio-maxillofacial surgical instrument and/or general surgical instrument may comprise the steps of placing a surgical tool of the surgical instrument into the recess of the registration and identification tool, pivoting the surgical instrument relative to the marker member, while the surgical tool is placed inside the recess, performing a detecting process of the relative movement of the surgical instrument, and identifying geometrical characteristics of the surgical tool and/or registering the relative position of the surgical tool to the remainder of the surgical instrument using the results of the detecting process.

The use of the registration and identification tool for registration and/or identification of a dental and/or cranio-maxillofacial surgical instrument and/or general surgical instrument of the invention is using the registration and identification tool or the registration and identification system of the invention. Therefore, the further features disclosed in connection with the above description of the registration and identification tool and the registration and identification system may also be applied to the method of the invention. The same applies to the use of the registration and identification tool.

BRIEF DESCRIPTION OF THE DRAWINGS

Hereinafter, non-limiting examples of the invention are explained with reference to the drawings, in which.

DETAILED DESCRIPTION OF CURRENTLY PREFERRED EMBODIMENTS

Figure 1:
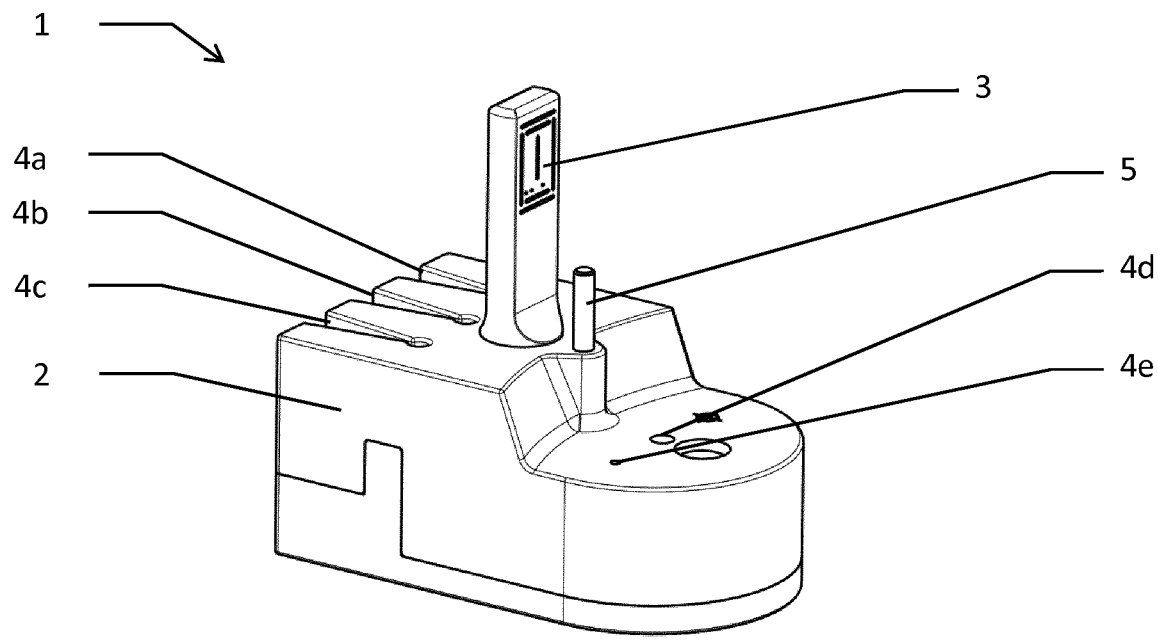
FIG. 1 shows a schematic perspective view of a registration and identification tool according to an embodiment of the present invention.

FIG. 1 shows a schematic perspective view of a registration and identification tool according to a currently preferred embodiment of the present invention.

The registration and identification tool 1 for a dental and/or cranio-maxillofacial surgical instrument and/or general surgical instrument 100, comprises a body 2, a marker member 3 which is optically detectable, the marker member 3 being detachably provided on the body 2, and a plurality of recesses 4a-e in the body 2, each of which extends from an outer surface of the body 2 into the inside of the body 2, thereby defining an extension direction of each of the recesses 4a-e, wherein each of the recesses 4a-e has a shape such that a lateral extension of the recess 4a-e decreases in the direction from the outer surface of the body 2 towards the inside of the body 2. The different recesses 4a-e and their purposes will be explained in detail below.

Moreover, the registration and identification tool 1 comprises a reference pin 5 which is provided in front of the marker element 3.

Figure 4:
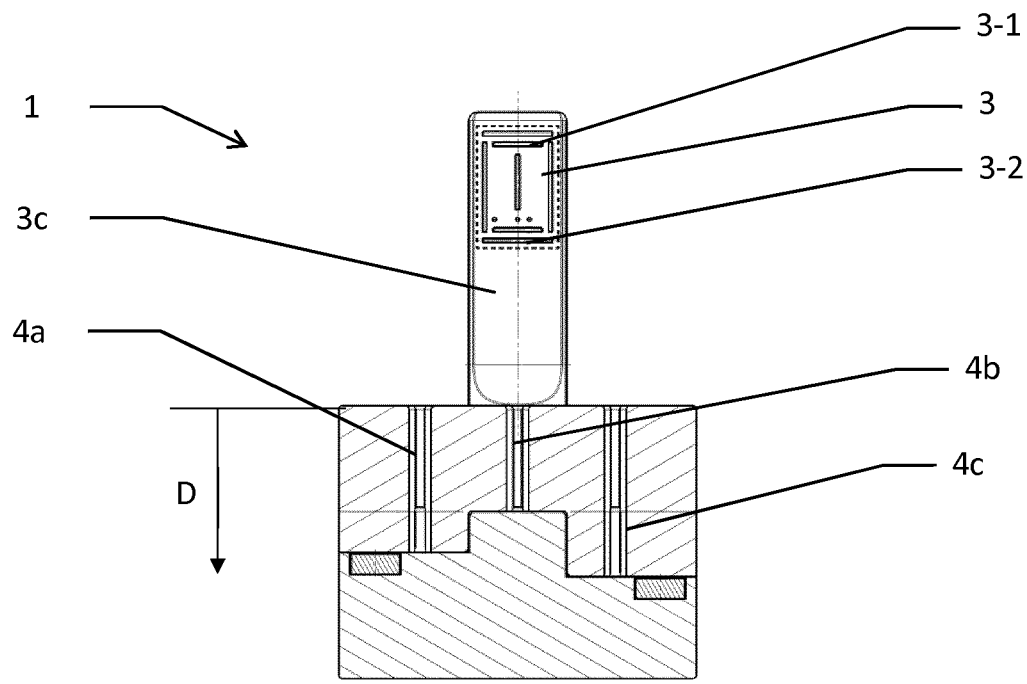
FIG. 4 shows a schematic cross-sectional view from the left side of the registration and identification tool shown in FIG. 1.

As shown in FIG. 4, which shows a schematic cross-sectional view from the left side of the registration and identification tool shown in FIG. 1, the marker element 3 comprises a plurality of marker elements 3-1, 3-2 which are arranged in a two-dimensional pattern, thereby defining a marker member plane 3c.

Figure 2:
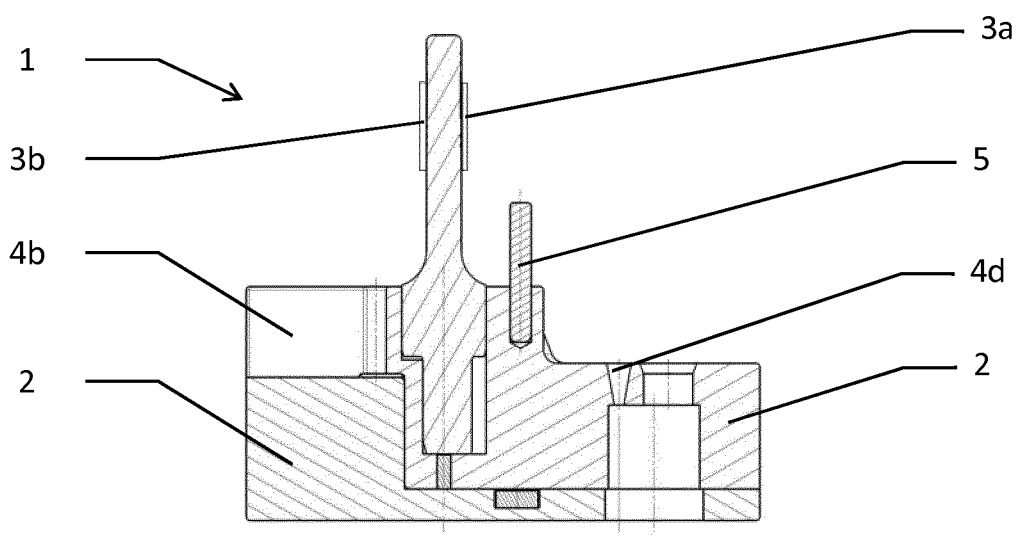
FIG. 2 shows a schematic cross-sectional view of the registration and identification tool shown in FIG. 1.

In FIG. 2, which shows a schematic cross-sectional view of the registration and identification tool shown in FIG. 1, it is recognizable that the registration and identification tool 1 comprises two marker elements 3a and 3b. The two marker elements 3a and 3b are provided on two opposite sides of the marker element 3 which are parallel to each other.

Further, the marker element 3 is placed substantially in the centre of the body 2, thereby dividing the body 2 in a front and a rear part. On the front part of the body 2 which has a substantially semi-circular shape, the reference pin 5 and two recesses 4d and 4e of the recesses 4a-e are provided. On the rear part of the body 2 the three recesses 4a to 4c of the recesses 4a-e are provided. The reference pin 5 and the recess 4d are both provided in the middle of the body 2 in the widthwise direction of the body 2. The recesses 4a to 4c are provided symmetrically to the middle of the body 2 in the widthwise direction of the body 2, wherein the central recess 4b of the recesses 4a to 4c is provided in the middle of the body 2 in the widthwise direction.

As can be taken from FIG. 2, the recess 4d is rather short in the extension direction of the recess, in particular shorter than the recesses 4a to 4c and has a conical shape in an extension direction of the recess 4d. In the shown embodiment, the extension direction of the recess 4d corresponds to the vertical direction of FIG. 2.

Figure 3:
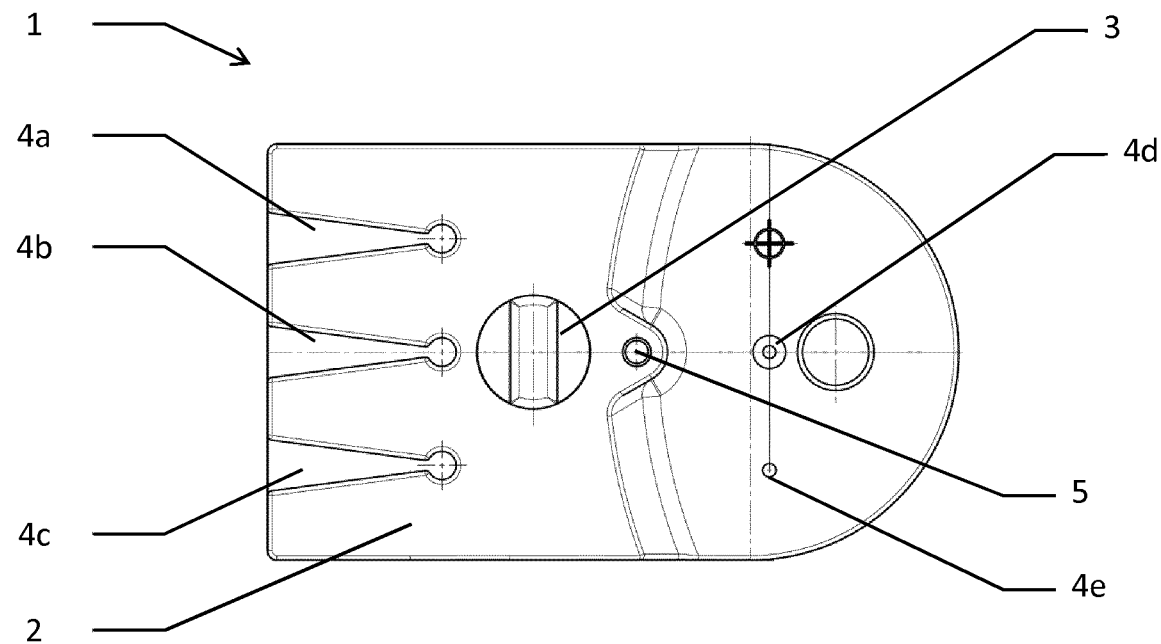
FIG. 3 shows a top schematic view of the registration and identification tool shown in FIG. 1.

Moreover, as shown in FIGS. 2 and 4, the recesses 4a to 4c are each provided with a substantially planar bottom, wherein the planar bottom of each of the recesses 4a to 4c is parallel to a planar bottom of the body 2 and substantially perpendicular to the marker element plane 3c. Additionally, as can be seen in FIGS. 2 and 3, the recesses 4a to 4c are open to two outer surfaces of the body 2, wherein the two outer surfaces of the body 2 are substantially perpendicular to each other. However, the two recesses 4d and 4e are only open to one outer surface of the body 2, in particular open to a top surface of the body 2.

Accordingly, the extension direction of the recesses 4d and 4e is parallel to the marker element plane 3c. On the other hand, as can be seen, in particular, in FIG. 3, the extension direction of the recesses 4a to 4c is substantially perpendicular to the marker member plane 3c. Hence, the extension direction of the recesses 4a to 4c is substantially perpendicular to the extension direction of the recesses 4d and 4e.

Moreover, the recesses 4a to 4c have a wedge shape, as can be seen in FIG. 3, which means the recesses are constituted by two substantially planar surfaces that are arranged opposite to each other at an angle relative to each other and a distance between the two planar surfaces decreases along the extension direction of the recess, in particular from left to right in the view of FIG. 3.

In the context of the present invention, the extension direction of the recesses 4a to 4e defines the direction of each of the recesses 4a to 4e, in which the respective recess 4a-e has shape such that in the extension direction of the recesses 4a to 4e the lateral extension of the recesses 4a to 4e decreases.

Accordingly, the lateral extension of the recesses 4d and 4e decreases in the vertical direction, in particular in the top-bottom direction in the view of FIG. 2 and the lateral extension of the recesses 4a to 4c decreases in the horizontal direction, in particular in the left-right direction in the view of FIGS. 2 and 3.

Moreover, as shown in FIG. 4, the three recesses 4a to 4c have different depths from the outer surface of the body 2, in particular from the top surface in a direction that is substantially perpendicular to the extension direction of the recess 4a to 4c and substantially perpendicular to the marker member plane 3c.

Figure 5:
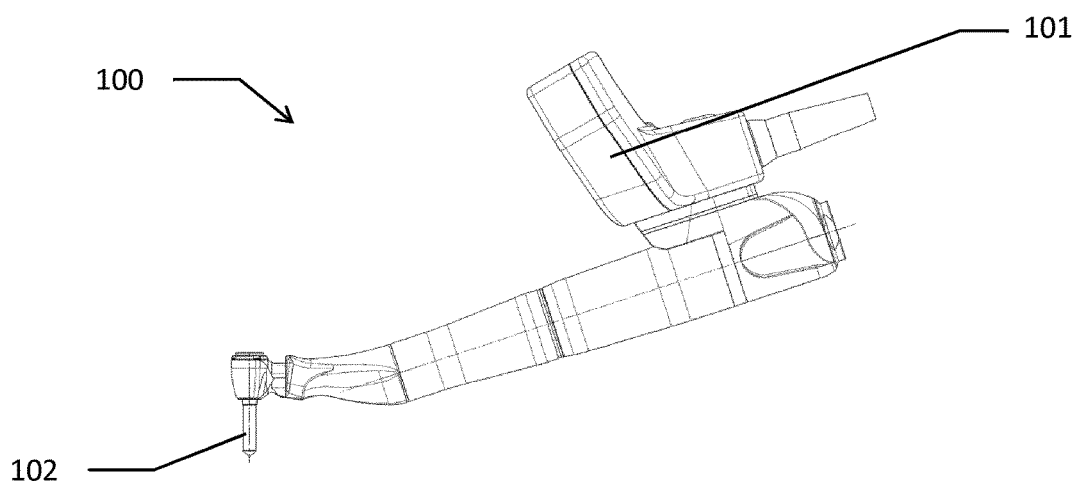
FIG. 5 shows a schematic front view of a surgical instrument which forms part of a navigations system according to an embodiment of the present invention.

FIG. 5 shows a schematic front view of a surgical instrument 100 which forms part of the above described navigations system. The surgical instrument 100 comprises the imaging unit 101 which forms part of the registration and identification system. Moreover, the surgical instrument 100 and the imaging unit 101 form part of the navigation system of the invention. Moreover, said registration and identification system further comprises a processing unit (not shown).

Figures 6A, 6B:
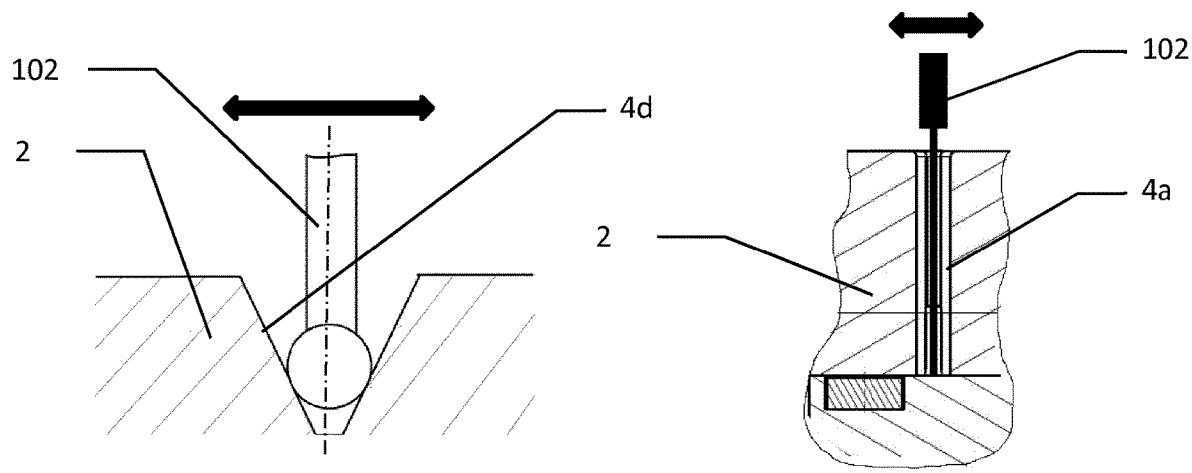
FIGS. 6a and 6b show illustrations of the use of the recesses 4a and 4d for the registration and/or identification of a dental drill according to a method/use of an embodiment of the present invention.

FIGS. 6a and 6b show illustrations of the use of the recesses 4a and 4d for the registration and or identification of a surgical tool, namely a dental drill 102.

As shown in FIG. 6a, a dental drill 102 with a spherical tip is inserted into the conical recess 4d. Since the recess 4d is conical and the outer diameter of the spherical tip of the dental drill 102 is bigger as the smallest lateral extension of the recess 4d, the dental drill 102 cannot be inserted fully into the recess 4d. In other words, the spherical surface of the spherical tip comes substantially in line contact with the surface of the conical recess 4d, wherein the line contact has substantially a circular shape.

As the conical shape of the recess 4d is known, in particular the diameter of the recess 4d in relation to the distance from the outer surface of the body 2, it is possible to determine or calculate the diameter of the spherical tip of the dental drill 102 when it is known how deep the centre of the spherical tip was inserted into the conical recess 4d.

FIG. 6a additionally shows, that in case of a dental drill 102 with a spherical tip or with a cylindrical tip (not shown) the dental drill 102 can be substantially pivoted in two spatial directions and rotated in one spatial direction which is perpendicular to the other two spatial directions.

Accordingly, it is possible to pivot the surgical instrument 100, into which the dental drill 102 is inserted, in two spatial directions, while the tip of the dental drill 102 is placed in the recess 4d. Hence, it is possible to pivot the surgical instrument relative to the marker member 3 and performing simultaneously a detecting process of the relative movement of the surgical instrument, in particular by an imaging unit 101 of the surgical instrument 100.

On the other hand, FIG. 6b shows the use of the recesses 4a to 4c, in particular the use of the recess 4a. As shown in FIG. 4a, the recesses 4a to 4c are intended for the use of registering and/or identifying surgical tool tools 102, in particular dental drills, with a cylindrical shape or a conical shape (not shown). In order to adjust the depth of the recess 4a-c to the length of the cylindrical tip of the dental tool 102, the recesses 4a to 4c are provided with different depths, as explained before with respect to FIG. 4. Accordingly, it can be avoided that the tip of the dental tool 102 cannot reach the bottom of the recess 4a-c or the length of the tip of the cylindrical head is too long so a large part of the tip cannot be inserted into the recess 4a-c, which would lead to instability and wrong measurement and/or detection results.

As the tapered shape of the recess 4a to 4c is known, in particular the lateral extension of the recesses 4a-c in relation to the distance from the outer surface of the body 2 (left outer surface of the body 2 in FIG. 3), it is possible to determine or calculate the diameter of the cylindrical tip of the dental drill 102 when it is known (detected by the imaging unit, will be explained in detail with respect to FIG. 7 below) how deep the centre of the cylindrical tip was inserted into the tapered recesses 4a-c. In other words, the diameter of the cylindrical tip of the dental drill 102 is determined based on how far the centre of the cylindrical tip could be inserted from the left side of the body 2 to the right side thereof.

Moreover, in case a drill head 102 with a conical shape is placed or inserted into the recesses 4a to 4c, when monitoring the pivoting of the drill head 102 about a tilted axis, which is substantially perpendicular the marker member plane 3c and substantially parallel to the extension direction of the recesses 4a to 4c, it becomes possible to determine the angle of the conical shape of the drill head 102.

Figure 7A:
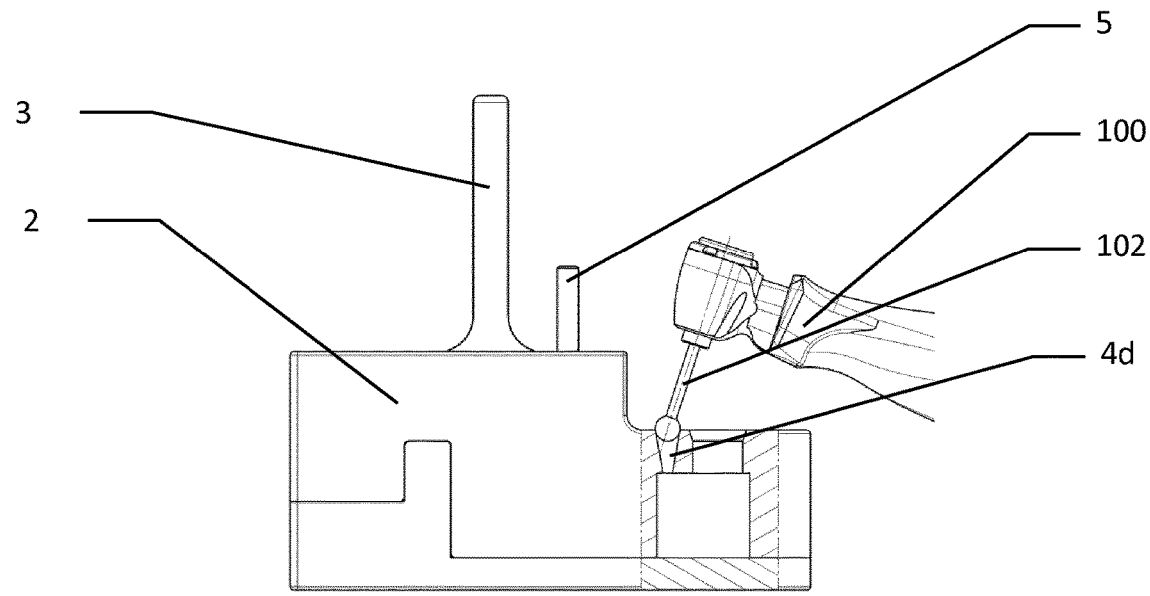
FIGS. 7a and 7b show illustrations of the use of the recesses 4a and 4d for registration and/or identification of a dental drill according to a method/use of an embodiment of present invention in a schematic cross-sectional view from the front side.
Figure 7B:
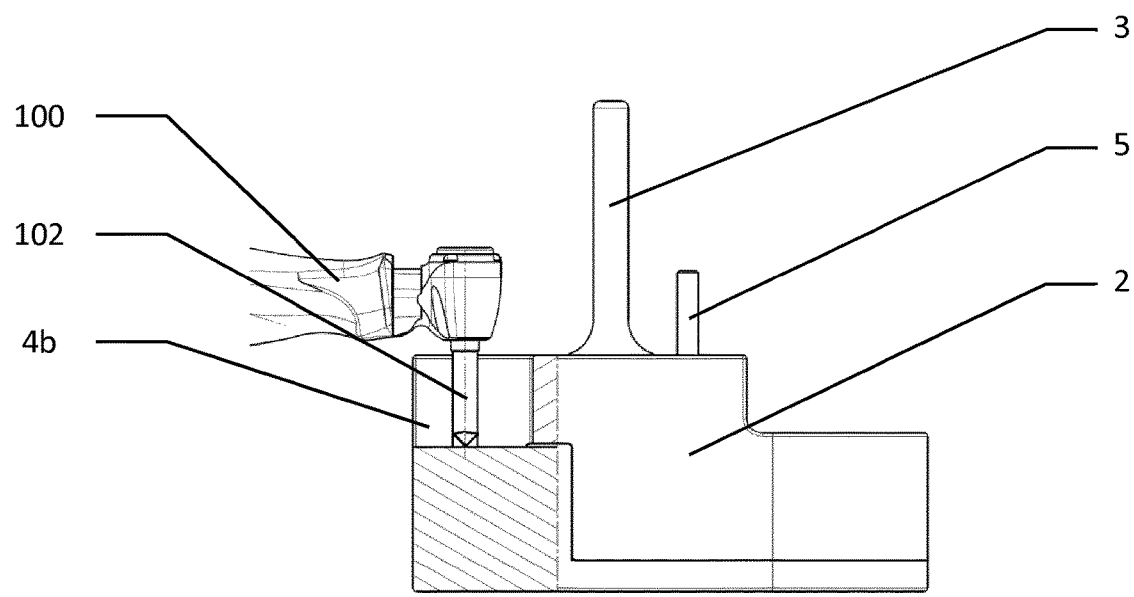

FIGS. 7a and 7b show illustrations of the use of the recesses 4a and 4d for registration and/or identification of a dental drill according to a method/use of an embodiment of present invention in a schematic cross-sectional view from the front side. As can be seen in both FIGS. 7a and 7b, because of the positional arrangement of the recesses 4a to 4e, the respective recess 4a-e is always easily accessible from the top of the body 2 and the surgical instrument 100 can be held during the registration and identification of the dental tool 102 in a comfortable substantially horizontal position. Moreover, as the recesses 4a to 4e are accessible from the top, the correct placement of the dental tool 102 into the respective recess 4a-e can easily be visually inspected and/or monitored.

Figure 8:
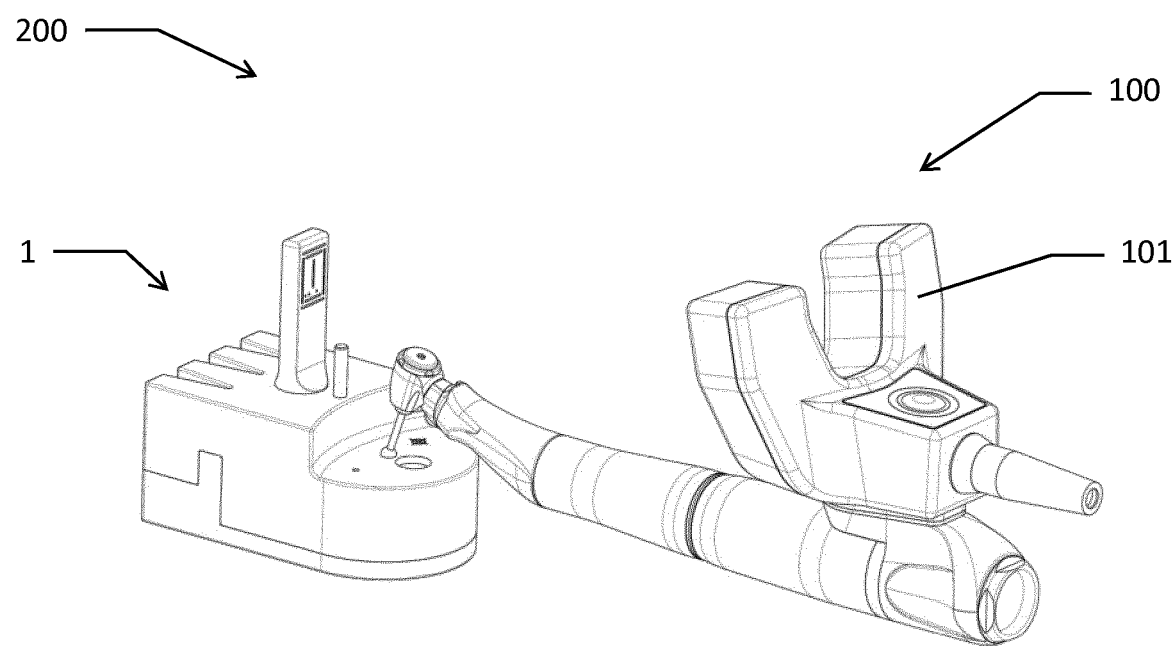
FIG. 8 shows a schematic perspective view of a navigation system according to an embodiment of the present invention.

FIG. 8 shows a schematic perspective view of a navigation system 200 according to an embodiment of the present invention. The navigation system 200 comprises the surgical instrument 100 and the registration and identification tool 1.

Moreover, the navigation system 200 comprises the imaging unit 101 which forms part of the registration and identification system.

Figure 9:
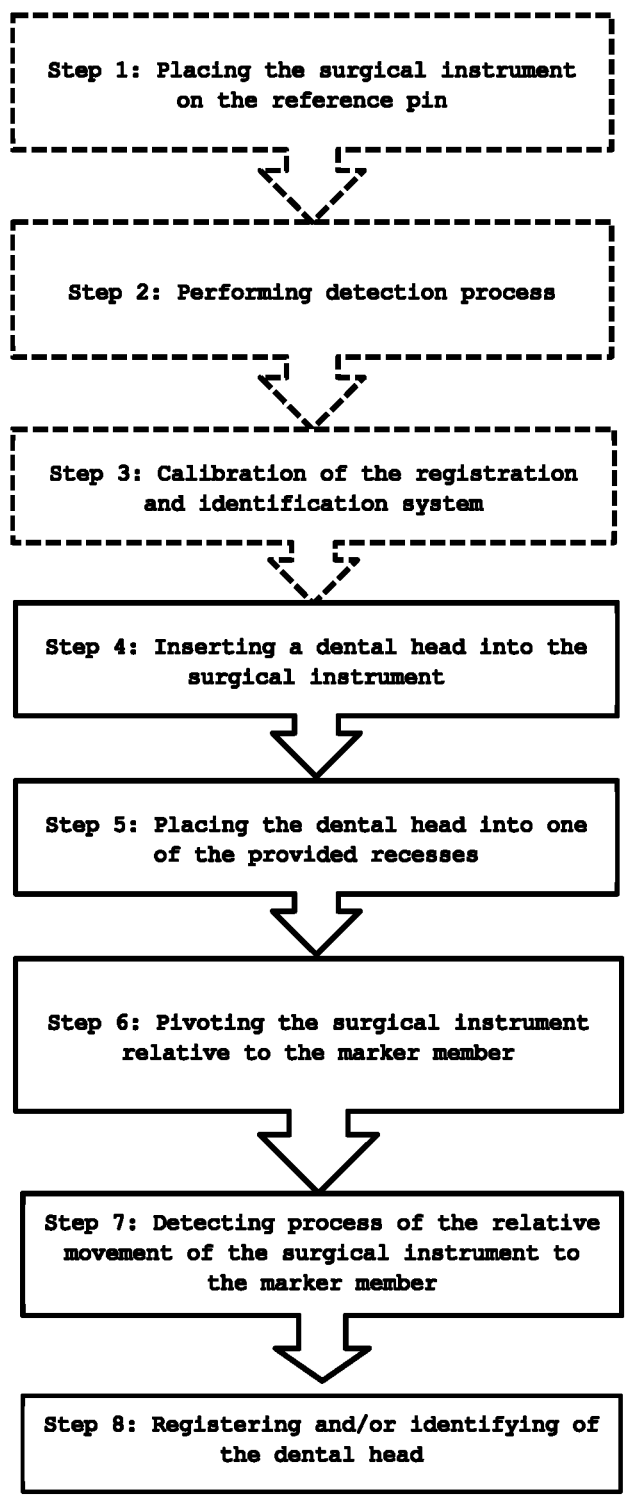
FIG. 9 shows a block-diagram illustrating a method for registration and/or identification of a dental drill according to an embodiment of present invention.

FIG. 9 shows a block-diagram illustrating a method for registration and/or identification of a dental drill according to an embodiment of present invention.

In the following the method for registration and/or identification of a dental drill will be described by referring to the block-diagram shown in FIG. 9.

In order to enable the registration and identification system, which comprises the registration and identification tool 1 and the imaging unit 101 which is attached to the surgical instrument 100, to register and/or identify an dental tool 102 which is inserted into the surgical instrument 100, it is necessary to perform a calibration of the registration and identification system.

Accordingly, at first the calibration process of the registration and identification system will be explained below. After the explanation of the calibration process the method for registering and identifying a surgical tool 102 by using the registration and identification system of present invention will be explained.

Calibration of the Registration and Identification System:

In step 1 of the calibration process of the registration and identification system, the empty surgical instrument 100 is placed onto the registration and identification system. In particular, no surgical tool 102 is installed (inserted) into the surgical instrument, that is, a tool holder of the surgical instrument 102 is empty. Hence, it is possible to place the tool holder of the surgical instrument 102 onto the reference pin 5 of the registration and identification tool 1, which is formed to correspond to a shaft of the surgical tool 102 that can be inserted into and clamped by the tool holder.

After placing the surgical instrument 100 with the tool holder onto the reference pin 5, step 2 of the calibration process is performed. In step 2, a detection process is performed. The detecting process can be performed during the surgical instrument 100 is not moved. In this way it is possible to calibrate the relative orientation and position between the imaging unit 101 and the marker member 3. Additionally, it is possible to determine (calculate) the relative orientation and position between imaging unit 101 and the tool holder of the surgical instrument 100.

However, it is also possible to perform the detecting process during the surgical instrument 100 is pivoted. Here and also in the following pivoting is performed preferably in a circular manner, that is, the surgical instrument is substantially circulated around a vertical axis, which is in case of the calibration process an axis that is coaxial with a longitudinal axis of the reference pin 5. In this way it is possible to teach the imaging unit 101/processing unit the influence of a relative movement (pivoting and/or circulating) of the surgical instrument 101 on the detecting results of the marker member 3.

In step 3 the calibration of the registration and identification system is performed using the detection results of the detecting process. After step 3 is completed, the registration and identification system is ready for use.

Registration and/or Identification of a Dental Tool

As after completing step 3 the system is ready for use, in step 4 for a dental tool 102 is inserted into the tool holder of the surgical instrument 100 and clamped.

In step 5 the surgical instrument 100 is placed again onto the registration and identification tool. In particular, the tip of the dental tool 102 is inserted into one of the recesses 4*a-e*. As the dental tool 102 of present example has a tip with a spherical shape, the dental tool 102 is placed into recess 4*d*.

In step 6 a pivoting of the surgical instrument 100 relative to the marker member 3 is performed, while the dental tool 102 is placed inside the recess 4*d*. As explained above, the dental tool 102 used in this example is a dental tool 102 with a spherical tip. Hence, it is necessary to perform step 6, in particular the pivoting. In case of a dental tool 102 with a cylindrical shape, in particular a dental tool 102 with a tip that has a cylindrical shape, it is not necessary to perform step 6, that is, it is not necessary to perform a pivoting of the surgical instrument 100.

In step 7 a detecting process of the relative movement of the surgical instrument 100 relative to the marker member 3 is performed.

After the detecting process of the relative movement is completed, step 8 is performed. In step 8 the registration and/or identification of the dental tool 102 is performed using the detection results of the detecting process. In particular, based on the detecting results of the detecting process the processing unit can determine the geometrical characteristics of the dental tool 102. Moreover, based on the detecting results of the detecting process it is also possible for the processing unit to determine the relative position of the dental tool 102 to the remainder of the surgical instrument 102.

The foregoing embodiments and their variants have been disclosed for illustrative purposes only, and further variation is wholly possible within the capabilities of the skilled reader. Accordingly, the appended claims are intended to cover all modifications, substitutions, alterations, omissions and additions which one skilled in the art could achieve from the foregoing disclosure, taking into account his own general and specialist knowledge and expertise.

The invention claimed is:

1. A registration and identification tool for a dental and/or cranio-maxillofacial surgical instrument, comprising:
a body having a first outer surface and a second outer surface substantially perpendicular to the first outer surface of the body,
a marker member which is optically detectable, the marker member being provided on the body,
a first recess in the body which extends from the first outer surface of the body into an inside of the body, thereby defining an extension direction of the first recess, wherein the first recess has a shape such that a lateral extension of the first recess decreases in the direction from the first outer surface of the body towards the inside of the body,
a second recess in the body, wherein the first and second recesses have different depths from one of the first and second outer surfaces of the body in a direction parallel to the other of the first and second outer surfaces of the body, and
a third recess in the body which extends from the second outer surface of the body into an inside of the body, thereby defining an extension direction of the third recess, wherein the third recess has a shape such that a lateral extension of the third recess decreases in the direction from the second outer surface of the body towards the inside of the body.

2. The registration and identification tool according to claim 1, wherein the marker member includes a plurality of marker elements arranged in at least one two-dimensional pattern, thereby defining at least one marker member plane.

3. The registration and identification tool according to claim 2, wherein the third recess has a conical shape in the extension direction of the third recess, which is substantially parallel to the marker member plane.

4. The registration and identification tool according to claim 2, wherein the extension direction of the first recess is substantially perpendicular to the marker member plane.

5. The registration and identification tool according to claim 1, wherein the first and second recesses have different depths in a direction perpendicular to the extension direction of the first recess.

6. The registration and identification tool according to claim 2, wherein a center of the first recess is located on or extends along a virtual line that is substantially perpendicular to the marker member plane and intersects the marker member centrically in a widthwise direction.

7. The registration and identification tool according to claim 2, further comprising a reference pin, wherein a center of the reference pin is located on a virtual line that is perpendicular to the marker member plane and intersects the marker member centrically in a widthwise direction.

8. The registration and identification tool according to claim 1, wherein the surgical instrument includes a drill or a milling cutter.

9. The registration and identification tool according to claim 1, wherein the marker member is detachable from the body.

10. The registration and identification tool according to claim 2, wherein the plurality of marker elements is configured to be detectable by one or more stereoscopic camera units, and/or one or more 3D scanners of an imaging unit.

11. The registration and identification tool according to claim 2, wherein the plurality of marker elements includes a first set of marker elements located on a first surface of the marker member and a second set of marker elements located on a second surface of the marker member that is opposite and substantially parallel to the first surface.

12. The registration and identification tool according to claim 11, wherein the first set of marker elements is arranged in a first two-dimensional pattern and the second set of marker elements is arranged in a second two-dimensional pattern, wherein the first and second two-dimensional patterns are different from each other.

13. The registration and identification tool according to claim 1, wherein the first recess and the second recess extend from the first outer surface of the body into the inside of the body.

14. The registration and identification tool according to claim 1, wherein the first recess is open to the second outer surface of the body.

* * * * *